United States Patent

Ebel et al.

[11] Patent Number: 5,831,097
[45] Date of Patent: Nov. 3, 1998

[54] PROCESS FOR THE PREPARATION OF ACYLOINS

[75] Inventors: Klaus Ebel, Lampertheim; Regina Schneider, Fussgönheim; Johann-Peter Melder, Mannheim; Joaquim Henrique Teles, Ludwigshafen, all of Germany

[73] Assignee: BASF Aktiengesellschaft, Ludwigshafen, Germany

[21] Appl. No.: 776,106

[22] PCT Filed: Jul. 8, 1995

[86] PCT No.: PCT/EP95/02660

§ 371 Date: Jan. 21, 1997

§ 102(e) Date: Jan. 21, 1997

[87] PCT Pub. No.: WO96/02484

PCT Pub. Date: Feb. 1, 1996

[30] Foreign Application Priority Data

Jul. 19, 1994 [DE] Germany ............ 44 25 436.9

[51] Int. Cl.⁶ .................... C07C 45/45; C07D 249/08
[52] U.S. Cl. ................ 548/262.2; 568/463; 568/464
[58] Field of Search .................. 568/463, 464; 548/262.2

[56] References Cited

U.S. PATENT DOCUMENTS

| | | |
|---|---|---|
| 3,957,888 | 5/1976 | Reiss et al. . |
| 4,035,395 | 7/1977 | Stetter et al. . |
| 4,482,696 | 11/1984 | Schuster et al. . |
| 5,386,062 | 1/1995 | Teles et al. ............ 568/463 |

FOREIGN PATENT DOCUMENTS

| | | |
|---|---|---|
| 219 317 | 4/1987 | European Pat. Off. . |
| 252 162 | 1/1988 | European Pat. Off. . |
| 364 752 | 9/1989 | European Pat. Off. . |
| 75 24178 | 2/1976 | France . |
| 42 30 466 | 9/1992 | Germany . |

OTHER PUBLICATIONS

Tetrahedron Letters, vol. 21, pp. 4517–4520, (1980).
J. Am. Chem. Soc., vol. 80, pp. 3719–3726, (1958).
J. Chem. Soc., Perkin II, pp. 310–316.

Primary Examiner—Johann Richter
Assistant Examiner—Jane C. Oswecki
Attorney, Agent, or Firm—Keil & Weinkauf

[57] ABSTRACT

A process for the preparation of acyloins of the general formula I

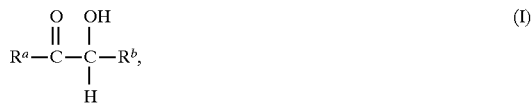

in which $R^a$ and $R^b$ are the same or different and stand for hydrogen or an optionally substituted $C_1$–$C_{20}$alkyl, an optionally substituted $C_6$–$C_{10}$aryl, an optionally substituted $C_7$–$C_{12}$aralkyl, an optionally substituted heteroaryl, or an optionally substituted heterocycloalkyl group, except for autocondensation products of formaldehyde, wherein an aldehyde of the formula II $$R^aCHO, \qquad (II)$$

is reacted, in the presence of a catalyst, with an aldehyde of the formula III $$R^bCHO, \qquad (III)$$

in which $R^a$ and $R^b$ have the above meanings and at least one of the radicals $R^a$ and $R^b$ denotes a radical other than hydrogen, which have been produced, with the assistance of an auxiliary base, from a triazolium salt of the formula IV

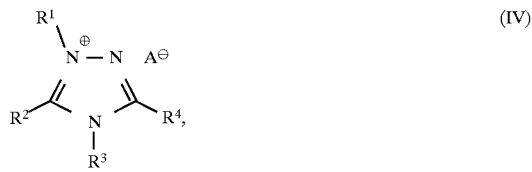

12 Claims, No Drawings

PROCESS FOR THE PREPARATION OF ACYLOINS

This application is a 371 of PCT/EP95/02660 filed Jul. 8, 1995.

DESCRIPTION

The present invention relates to a process for the preparation of acyloins of the general formula I

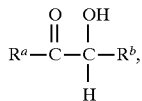     (I)

in which $R^a$ and $R^b$ are the same or different and stand for hydrogen or an optionally substituted $C_1$–$C_{20}$ alkyl, an optionally substituted $C_6$–$C_{10}$ aryl, an optionally substituted $C_7$–$C_{12}$ aralkyl, an optionally substituted heteroaryl, or an optionally substituted heterocycloalkyl group, except for autocondensation products of formaldehyde.

In addition, the present invention relates to a process for the preparation of cycloaliphatic or heterocycloaliphatic acyloins having a total of from 5 to 12 ring members.

In addition, the present invention relates to a process for the preparation of acyloins of the general formula Ia

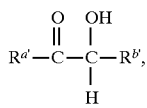     (Ia)

in which the radicals $R^{a'}$ and $R^{b'}$ are different and stand for hydrogen or an optionally substituted $C_1$–$C_{20}$ alkyl, an optionally substituted $C_6$–$C_{10}$ aryl, an optionally substituted $C_7$–$C_{11}$ aralkyl, an optionally substituted heteroaryl, or an optionally substituted heterocycloalkyl group, except for autocondensation products of formaldehyde.

Since the publication of papers by Breslow (*J. Am. Chem. Soc.* 80, 3719 (1959)) it is known that thiazolium ylides can be used as catalysts for the catalytical reversal of polarization of aldehydes and thus for their condensation to form acyloins. Castells (*Tetrahedron lett.* 21, 4517 (1980)) applied this reaction to the autocondensation of formaldehyde. α-hydroxycarbonyl compounds are generally designated as acyloins, in particular α-hydroxyketones and α-hydroxyaldehydes. The said processes have considerable disadvantages however. Thus relatively large amounts of the thiazolium ylide serving as catalyst, that is to say from 5 to 20 mol %, based on the aldehyde used, are required in order to achieve a satisfactory space-time yield. In addition, the thiazolium ylide catalysts have been found to be relatively unstable during continuous operation, ie they form considerable quantities of decomposition products of the thiazolium ylide catalyst which are virtually impossible to separate from the desired product. These factors are an obstacle to the use of the thiazolium ylide catalysts in industrial processes.

DE-A 4,230,466 relates to a process for the preparation of autocondensation products of formaldehyde by means of triazolium salt catalysts. Formaldehyde used in this process as starting material is the simplest of the aldehydes but is unique, as aldehyde, in respect of its chemical behavior, particularly as regards its high chemical reactivity. The same applies, on account of their special chemical structure, to the formaldehyde/triazolium salt adducts formed as intermediates in this process. In addition, in the condensation of formaldehyde with itself there is virtually no sterical hindering of the reactants. This document makes no reference to the applicability of this process to the condensation of aldehydes higher than formaldehyde.

Acyloins are very well suited, on account of their bifunctionality (carbonyl and hydroxy group in mutual α-position relationship), for the synthesis of heterocyclics, in particular imidazoles (EP-A 252,162) and imidazolones (*J. Chem. Soc.* Perkin II, 310 (1981)), which are in turn used, eg, in the preparation of medicines and plant protectants and are thus desirable intermediates and building blocks for the preparation of such active materials. On account of their high reducing power, acyloins are used as reducing agents in the dyeing industry, for example for dyeing textile materials consisting of cellulose fibers (EP-A 364,752). Further applications of acyloins are given below by way of example:

Acetoin is used, eg, as an aromatic substance in foodstuffs, likewise the diacetyl obtainable therefrom by oxidation. Furoin serves as starting material for the preparation of furildioxime, which is obtained therefrom by its oxidation to form furil and its subsequent oximization with hydroxylamine and is used as a reagent for the analytical determination of heavy metal cations, for example nickel ions. Benzoin is, for example, the immediate precursor in the preparation of benzil, which can be used pharmaceutically as a virus staticum and also serves as a starting material for the preparation of antimycotics and preservatives.

It was thus the object of the present invention to provide a process for the preparation of acyloins from the corresponding readily available aldehydes, which process does not suffer from the drawbacks of the thiazolium ylide-catalyzed preparation of acyloin. Furthermore the process is desirably capable of economically providing so-called crossed acyloins, ie acyloins which are formed by condensation of two different aldehydes.

Accordingly, there has been found a process for the preparation of acyloins of the general formula I

     (I)

in which $R^a$ and $R^b$ are the same or different and stand for hydrogen or an optionally substituted $C_1$–$C_{20}$ alkyl, an optionally substituted $C_6$–$C_{10}$ aryl, an optionally substituted $C_7$–$C_{12}$ aralkyl, an optionally substituted heteroaryl, or an optionally substituted heterocycloalkyl group, except for autocondensation products of formaldehyde, wherein an aldehyde of the formula II

     $R^a$CHO,     (II)

is caused to react, in the presence of a catalyst, with an aldehyde of the formula III

     $R^b$CHO,     (III)

in which $R^a$ and $R^b$ have the above meanings and at least one of the radicals $R^a$ and $R^b$ denotes a radical other than hydrogen, which have been produced, with the assistance of an auxiliary base, from triazolium salts of the formula IV

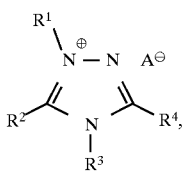
(IV)

in which

R¹ and R³ are the same or different and stand for aliphatic groups having from 1 to 30 carbon atoms, optionally substituted aryl groups, optionally substituted aralkyl groups and/or optionally substituted heteroaryl groups, R² denotes hydrogen or the group R$^b$CH(OH)

and in which

R⁴ denotes hydrogen, a halogen atom, a nitro or cyano group, an aliphatic group having from 1 to 30 carbon atoms, an optionally substituted aryl group, an optionally substituted aralkyl group, an optionally substituted heteroaryl group, an alkoxy group —OR⁵, a thioether group —SR⁶, an amino group —NR⁷R⁸, an acyl group —COR⁹ or an ester group —COOR¹⁰, where the radicals R⁵, R⁶, R⁷, R⁸, and R⁹ stand for radicals as mentioned above with respect to R¹, and R¹⁰ is a $C_1$–$C_{30}$ alkyl or an optionally substituted aryl or aralkyl group, or in which R³ and R⁴ together form a $C_3$–$C_5$ alkylene, $C_3$–$C_5$ alkenylene, $C_6$–$C_{14}$ arylene, $C_7$–$C_{14}$ aralkylene, or $C_8$–$C_{14}$ aralkenylene bridging member, and A is the equivalent of an anion carrying one or more negative charges for the electrical neutralization of the charge on the triazolium cation.

There has also been found a process for the preparation of cycloaliphatic or heterocycloaliphatic acyloins having a total of from 5 to 12 ring members, wherein an optionally substituted aliphatic $C_5$–$C_{12}$ dialdehyde or a heteroaliphatic dialdehyde having a chain length of from 4 to 11 carbon atoms, which additionally contains in the chain an —O—, —S— or —N(R$^c$)— group, in which R$^c$ is a $C_1$–$C_4$ alkyl or acyl group, is caused to react with a catalyst as defined in any of claims 1 to 6.

In addition, there has been found a process for the preparation of crossed acyloins of the general formula Ia

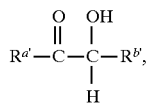
(Ia)

in which

R$^{a'}$ and R$^{b'}$ differ from each other and stand for hydrogen or an optionally substituted $C_1$–$C_{20}$ alkyl, an optionally substituted $C_6$–$C_{10}$ aryl, an optionally substituted $C_7$–$C_{12}$ aralkyl, an optionally substituted heteroaryl, or an optionally substituted heterocycloalkyl group, except for dihydroxy acetone, glyceryl aldehyde, and $C_4$ and $C_5$ sugars, wherein an aldehyde of the formula II

(II)

is caused to react with a triazolium salt of the formula IVa

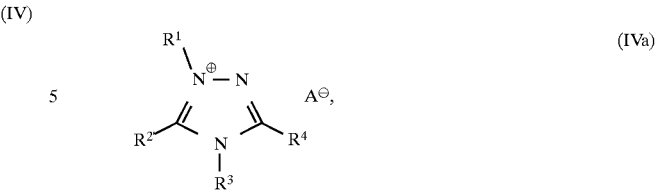
(IVa)

in which

R¹ and R³ are the same or different and stand for aliphatic groups having from 1 to 30 carbon atoms, for optionally substituted aryl groups, for optionally substituted aralkyl groups, and/or for optionally substituted heteroaryl groups, R$^{2'}$ represents the group R$^b$CH(OH), and in which R⁴ is the same as, or different from, the radicals R¹ and R³ or denotes hydrogen, a halogen atom, a nitro or cyano group, an aliphatic group having from 1 to 30 carbon atoms, an optionally substituted aryl group, an optionally substituted aralkyl group, an optionally substituted heteroaryl group, an alkoxy group —OR⁵, a thioether group —SR⁶, an amino group —NR⁷R⁸, an acyl group —COR⁹, or an ester group —COOR¹⁰, where the radicals R⁵, R⁶, R⁷, R⁸ and R⁹ stand for radicals as mentioned above with respect to R¹ and R¹⁰ is a $C_1$–$C_{30}$ alkyl or an optionally substituted aryl or aralkyl group, or in which R³ and R⁴ together form a $C_3$–$C_5$ alkylene, $C_3$–$C_5$ alkenylene, $C_6$–$C_{14}$ arylene, $C_7$–$C_{14}$ aralkylene, or $C_8$–$C_{14}$ aralkenylene bridging member, and A is the equivalent of an anion carrying one or more negative charges for the electrical neutralization of the charge on the triazolium cation, in the presence of an auxiliary base and in a molar ratio of triazolium salt IVa to aldehyde II of from 1:1 to 5:1, provided that at least one of the radicals R$^a$ and R$^b$ is not hydrogen.

The process of the invention thus relates to the preparation of acyclic or cyclic acyloins, with the exception of the preparation of autocondensation products of formaldehyde as produced by the reaction of formaldehyde with catalysts of the formula IV or V, ie, for example, glycolaldehyde, glyceryl aldehyde, dihydroxy-acetone and $C_4$ and $C_5$ sugars. When the process of the invention relates to the preparation of acyclic acyloins, both so-called uniform acyloins can be prepared by condensation of two aldehydes R$^a$CHO II and R$^b$CHO III, in which the radicals R$^a$ and R$^b$ are the same but are not hydrogen, and so-called crossed acyloins can be produced by condensation of two different aldehydes R$^a$CHO II and R$^b$CHO III.

The catalysts that can be used in the present invention are catalysts produced from 1,2,4-triazolium salts IV with the assistance of an auxiliary base. Since the radicals R¹, R³ and R⁴ usually have an influence only on the solvency of the triazolium salts, these radicals can have a large number of meanings.

Thus R¹, R³ and R⁴ can be the same or different and stand for aliphatic groups having from 1 to 30 carbon atoms, such as $C_1$–$C_{30}$ alkyl, preferably $C_1$–$C_{10}$ alkyl groups, $C_2$–$C_{30}$, preferably $C_2$–$C_{10}$ alkenyl or alkynyl groups having one or two, preferably only one, multiple bond, $C_3$–$C_{20}$, preferably $C_3$–$C_{10}$ cycloalkyl or alkenyl groups, $C_3$–$C_{20}$ heterocycloalkyl or heterocycloalkenyl groups such as piperidinyl, piperazinyl, pyrrolidinyl, imidazolidinyl, tetrahydrothienyl, tetrahydrofuranyl, tetrahydropyranyl, thiazolidinyl, oxazolidinyl, imidazolinyl, thiazolinyl, oxazolynyl, or crown ether groups, $C_2$–$C_{30}$, preferably $C_2$–$C_{10}$ alkoxy groups attached via a carbon atom to the triazolium or tetrazolium ring and having one or more, preferably only one, oxygen atom in the ether chain, $C_1$–$C_{30}$, preferably $C_1$–$C_{10}$ haloalkyl groups having one or more, preferably from one to three, halogen atoms and containing fluorine, chlorine and/or bromine, preferably fluorine and/or chlorine, particularly fluorine, in the case of fluoroalkyl groups advantageous also perfluorinated fluoroalkyl groups, amino groups attached to the triazolium ring via a carbon atom, such as $C_2$–$C_{30}$, preferably $C_2$–$C_{10}$, secondary amino groups, $C_3$–$C_{30}$, preferably $C_3$–$C_{21}$ tertiary amino groups, optionally substituted aryl groups, preferably $C_6$–$C_{14}$ aryl groups, in particular phenyl, naphthyl, anthryl, or phenanthryl groups, optionally substituted $C_7$–$C_{20}$ aralkyl groups, particularly the benzyl, phenethylene, or naphthylmethylene group, or optionally substituted $C_2$–$C_{15}$ heteroaryl groups having from 1 to 3 nitrogen atoms or one oxygen or sulfur atom or having 1 or 2 nitrogen atoms or one oxygen or sulfur atom in the ring, such as the furanyl, thienyl, pyrrolyl, pyrazolyl, imidazolyl, oxazolyl, thiazolyl, isothiazolyl, isoxazolyl, pyridynyl, pyrimidynyl, pyrazynyl, quinolynyl, naphthyridynyl, 1,2,4-triazolyl, or acridynyl groups.

Both the aliphatic and the aromatic radicals and also, of course, the aralkyl radicals can be mono- or poly-substituted, preferably not more than trisubstituted, by halogen atoms or nitro, hydroxy, cyano, alkyl, alkoxy, or amino groups. Since these substituents usually have only a slight effect on the catalytic activity of the catalysts produced from IV or V, the unsubstituted radicals $R^1$, $R^3$, and $R^4$ mentioned above will preferably be used, mainly on account of the lower cost involved in their manufacture.

Apart from having the aforementioned meanings the radical $R^4$ can, unlike the radicals $R^1$ and $R^3$, be a hydrogen atom, a nitro or cyano group, a halogen atom selected from the group consisting of fluorine, chlorine, and bromine, an alkoxy group —$OR^5$ attached to the triazolium ring via the oxygen atom, a thioether group —$SR^6$ attached to the triazolium ring via the sulfur atom, an amino group —$NR^7R^8$ attached to the triazolium ring via the nitrogen atom, an acyl group —$COR^9$, or an ester group —$COOR^{10}$. The radicals $R^5$, $R^6$, $R^7$, $R^8$, and $R^9$ can have the same meanings as stated above for the radical $R^1$. Similarly to the radicals $R^1$, the radicals $R^5$, $R^6$, $R^7$, $R^8$, $R^9$, and $R^{10}$ can also carry the substituents cited for the radicals $R^1$, but preferably, on account of the lower manufacturing costs, unsubstituted radicals $R^5$, $R^6$, $R^7$, $R^8$, $R^9$, and $R^{10}$ will usually be chosen. Preferred radicals $R^5$, $R^6$, $R^7$, $R^8$, $R^9$, and $R^{10}$ are $C_1$–$C_{30}$ and particularly $C_1$–$C_{10}$ alkyl groups, $C_6$–$C_{10}$ aryl groups, particularly the phenyl or naphthyl group, and $C_7$–$C_{20}$ and preferably $C_7$–$C_{14}$ aralkyl groups, particularly the benzyl, phenethylene, or naphthylmethylene group. A further preferred radical $R^7$ is the hydroxymethylene group. Other preferred radicals $R^7$ are those which carry a hydroxy group in the α-position relative to the nitrogen atom.

The radical $R^4$ can form, furthermore, together with the radical $R^3$, a $C_3$–$C_5$ alkylene or $C_3$–$C_5$ alkenylene bridging member or a $C_6$–$C_{14}$ arylene bridging member, preferably an o-phenylene, o-naphthylene, 1,8-naphthylene, o-fluorenylene, 5,4-fluorenylene, o-phenanthrylene, 5,4-phenanthrylene, 9,10-phenanthrylene, o-anthrylene, 1,9-anthrylene, or a 2,2'-biphenylene bridging member, a $C_7$–$C_{14}$ aralkyl or $C_7$–$C_{14}$ aralkenylene bridging member, where these bridging radicals $R^3 \cap R^4$ can be mono- or poly-substituted, preferably not more than trisubstituted, by halogen atoms or nitro, hydroxy, cyano, alkyl, alkoxy, or amino groups. Since these substituents usually have only a slight effect on the catalytic activity of the relevant catalysts produced from IV, unsubstituted bridging radicals $R^3 \cap R^4$ are usually preferred, mainly on account of the lower cost involved in their manufacture. Since both the radical $R^3$ and the radical $R^4$ can contain the hetero atoms nitrogen, oxygen, or sulfur the bridging radical $R^3 \cap R^4$ can also contain these hetero atoms. The bridging radical $R^3 \cap R^4$ preferably contains not more than two, in particular not more than one, of said hetero atoms.

The radical $R^2$, which is present on the presumed catalytically active center of the trazolium compounds IV, can be hydrogen or the group $R^b CH(OH)$ in the case of the embodiments of the process of the invention involving the preparation of the acyloins of the formula I. The radical $R^2$ is preferably hydrogen. In the case of deliberate preparation of crossed acyloins of the formula Ia, the radical $R^2$ is preferably the group $R^b CH(OH)$. In the preparation of alicyclic or heterocycloaliphatic acyloins from the corresponding dialdehydes, the radical $R^2$ is preferably hydrogen.

Theoretically, the anions forming the anion equivalent A for electrical neutralization of the charge on the triazolium cation, can be chosen arbitrarily, but the non-nucleophilic anions of mineral acids or strong carboxylic acids are preferably used. These anions can carry one or more, preferably not more than three, negative charges. Such anions carrying a number of negative charges can electrically neutralize as many triazolium cations as correspond to the number of said negative charges and will attach themselves thereto electrostatically, ie, in the manner of a salt. Thus the anion equivalent A is the molar amount of an anion carrying one or more negative charges required for electrical neutralization of a molar amount of the triazolium cation divided by the charge number of said anion.

Suitable anions are, for example, the anions of halides, such as fluoride, chloride, bromide, or iodide, and nitrate, tetrafluoroborate, tetraphenylborate, hexafluorophosphate, hexachloroplatinate, perchlorate, sulfate, phosphate, trifluoroacetate, methanesulfonate, or toluenesulfonate anions. Likewise acid cation exchangers in their anionic form, for example polyacrylates, sulfonated phenol-formaldehyde resins, or sulfonated polystyrene, can act as polyanions. The anion used is preferably a halide, nitrate, tetrafluoroborate, or perchlorate.

The action of the triazolium salts IV used in the present invention is still extensively unknown and it is only possible to make conjectures as to the chemical mechanism underlying the process of the invention. The results of all previous experiments indicate, however, that the triazolium salt IV is deprotonized in position 5 of the triazolium ring by the auxiliary base to produce the ylide VI forming a mesomer with the carbene VII (cf equation (1)),

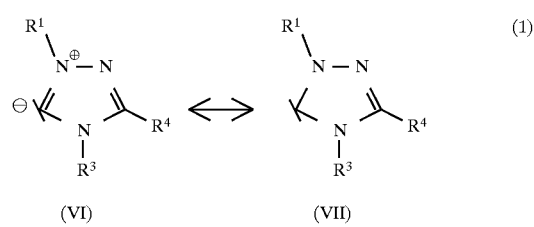

which is presumed to be the actual catalytically active species. It is possible that other catalytically active species of these triazolium compounds may be present under the reaction conditions, these being derivable from the ylide VI/carbene VII and in equilibrium therewith, but the prerequisite for the development of catalytic activity would seem to be the necessity of passing through the reactive intermediate stage triazolium ylide/carbene VI/VII irrespective of the manner in which this is generated or of the starting materials which are used for the purpose. However, these explanations are to be regarded only as an attempt at elucidation of the reaction of the invention. If future knowledge should show that reactive intermediate stages other than those postulated herein catalyze the reaction of the invention, this is to be regarded as being irrelevant to the scope of the present application, since these species are, in the last instance, produced by the measures of the invention.

An indication of the fact that position 5 of the triazolium ring is very probably the catalytically active center of these catalysts, is given by the fact that during the reaction of alcoholates, for example methanolates, or thiolates with the triazolium salts IV it is possible to isolate alcoholate or thiolate addition products of the formula V

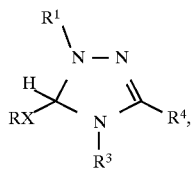
(V)

in which x stands for oxygen or sulfur, R is a $C_1$–$C_4$ alkyl group, preferably the methyl group, and $R^1$, $R^3$, and $R^4$ have the meanings stated above. If, instead of the triazolium salts IV, these addition compounds v are caused to react with the aldehydes II and III under the reaction conditions usually employed in the process of the invention, but in the absence of the auxiliary base, the acyloins I likewise form. Probably the alcohol or the thiol RXH is then again eliminated from the compounds V under the reaction conditions usually employed and the presumed catalytically active ylide VI or carbene VII, which can then display its catalytic activity.

It is also possible to heat the addition compounds V alone, in solid form, or in a high-boiling solvent and thus to eliminate the alcohol or the thiol concerned and thus to produce compounds which are particularly active catalysts for the condensation of the aldehydes II and III. Very probably the corresponding ylide VI or the corresponding carbene VII or a compound acting in an equivalent manner to these species is formed during this thermolysis.

Thus three types of embodiment result for the process of the invention for the preparation of acyloins I:

α) The use of the triazolium salt compounds IV as catalysts in the presence of an auxiliary base.

β) The use of the addition compounds V as catalysts.

γ) The use of thermolysis products obtained by thermal elimination of the alcohols ROH or thiols RSH from the addition compounds V, as catalysts.

Common to all of these three embodiments of the process of the invention is the fact that, in accordance with the above explanations, the condensation of the aldehydes II or III is catalyzed, in the last instance, by the same catalytically active species. All of these three embodiments are therefore equivalent to each other, although these process variants have three different advantages, which will be the determining factor in each individual case when selecting one or other of the variants.

Variant α) has the advantage that no further derivatives of the trazolium compounds IV are required. The variants β) and γ) have the advantage that they can be carried out in the absence of an auxiliary base. Since the presence of an auxiliary base in the reaction mixture can possibly be the cause of undesirable side reactions of the acyloins, this advantage is particularly important in certain cases. The catalytically active compounds used in accordance with variant γ) are particularly active catalysts. The methanolate addition compounds Va are particularly suitable for carrying out variant β) of the process of the invention.

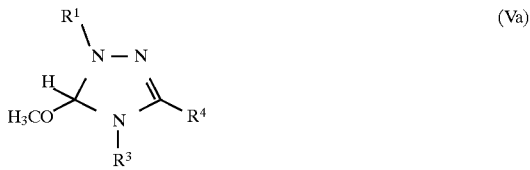
(Va)

The starting aldehyde $R^aCHO$ II or $R^bCHO$ III used in the process of the invention can be, theoretically, any desired aldehyde. The aldehydes $R^aCHO$ II and $R^bCHO$ III, which are caused to react with each other in the present invention to produce the corresponding acyloins, can be the same or different, the autocondensation of formaldehyde not being part of the process of the invention.

The starting aldehydes II and III used can, for example, be aliphatic, cycloaliphatic, aromatic, heteroaromatic, heterocycloaliphatic, and araliphatic aldehydes.

Although, theoretically, all aliphatic aldehydes can be used in the process of the invention, this is generally carried out using those aldehydes $R^aCHO$ II and $R^bCHO$ III in which the radicals $R^a$ and $R^b$ stand for $C_1$–$C_{20}$, preferably $C_1$–$C_{15}$ and more preferably $C_1$–$C_{10}$ alkyl groups. These alkyl groups can be straight-chained or branched-chained. Straight-chain aldehydes are preferably used. Of the aldehydes I and II having branched alkyl chains, those which are sterically hindered to a low degree are preferred. The alkyl groups of the aliphatic aldehydes can be unsubstituted or can carry from 1 to 3 identical or different, preferably one, substituent(s) inert under the reaction conditions. Such substituents are, for example, halogen atoms, such as fluorine, chlorine, bromine, or iodine atoms, preferably fluorine, chlorine or bromine atoms, the nitrile group, the nitro group, the oxo group, the hydroxy group, the thiol group, $C_1$–$C_{20}$, preferably $C_1$–$C_{10}$, particularly $C_1$–$C_4$ alkoxy groups, $C_6$–$C_{10}$ aryloxy groups, particularly the phenoxy group, $C_7$–$C_{12}$ aralkyloxy groups, particularly the benzyloxy group, cyclic or acyclic acetal groups, —COOR— groups, in which R is an aromatic, aliphatic, or araliphatic radical,

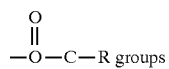
—O—C—R groups in which R is an aromatic, aliphatic or araliphatic radical, a di-($C_1$–$C_{10}$ alkyl), preferably di-($C_1$–$C_4$ alkyl) amino group, a $C_1$–$C_{10}$, preferably $C_1$–$C_4$ alkylthio group, a carboxylate, or a sulfonate group. Furthermore, said alkyl groups can contain C—C double or triple bonds.

Also, the radicals $R^a$ and $R^b$ can be cycloaliphatic groups, for example, $C_3$–$C_8$, preferably $C_3$–$C_6$ cycloalkyl groups, or heterocycloaliphatic groups having a total of from 5 to 8, in particular from 5 to 6 ring members, and these heterocycloaliphatic groups, depending on their ring size, can contain from one to three, preferably 1 or 2, in particular one, oxa, thia or (N-R)-diyl— groups, in which R is an alkyl, aryl, aralkyl, or acyl group. The cycloaliphatic or heterocycloaliphatic radicals $R^a$ and $R^b$ can be unsubstituted or can carry from one to three identical or different, preferably one, substituent(s). For example, the cycloaliphatic or heterocycloaliphatic radicals $R^a$ and $R^b$ can be substituted by those substituents listed above in respect of the aliphatic radicals $R^a$ and $R^b$. The substitution pattern of the cycloaliphatic or heterocycloaliphatic radicals $R^a$ and $R^b$ is not usually critically important with regard to the practicability of the process of the invention.

Preferred starting compounds $R^a$CHO II and $R^b$CHO III are also those in which the radicals $R^a$ and $R^b$ stand for $C_6-C_{10}$ aryl groups, for example the phenyl or naphthyl group. These aryl groups can be unsubstituted or can carry from one to three identical or different, preferably one, substituent(s). Suitable substituents of the aryl groups are, for example, those substituents mentioned above in respect of the aliphatic radicals $R^a$ and $R^b$. Of course, the aromatic radicals $R^a$ and $R^b$ can, if desired, be substituted by $C_1-C_{10}$, preferably $C_1-C_4$ alkyl groups apart from the loc. cit substituents. The substitution pattern of the aryl groups is not usually critically important with regard to the practicability of the process of the invention.

Furthermore, aralkylaldehydes can be used as starting compounds $R^a$CHO II and $R^b$CHO III in the process of the invention, preferably those in which $R^a$ and $R^b$ stand for $C_7-C_{12}$ aralkyl groups, particularly the benzyl group,. The $C_7-C_{12}$ aralkyl groups can be unsubstituted or can carry from one to three identical or different substituents. Since the degree of substitution and the substitution pattern of these aralkyl compounds are not generally of critical importance in determining whether the process of the invention can be carried out or not, these aralkyl radicals can be substituted in the manner disclosed in the previous paragraph with regard to the aryl radicals $R^a$ and $R^b$, for example, using the same substituents.

Another preferred starting material for use in the process of the invention can be a heteroaromatic aldehyde $R^a$CHO II or $R^b$CHO III. The nature of the heteroaromatic radicals $R^a$ and $R^b$ is not usually critically important with respect to the practicability of the process of the invention. In the process of the invention, use can be made of both heteroaromatic aldehydes rich in electrons, such as pyrrolcarbonal or furancarbonal (furfurol), and heteroaromatic aldehydes of low electron content, such as pyridinecarbonal. Examples of aromatic radicals $R^a$ and $R^b$ are the furyl, pyrrolyl, thienyl, imidazolyl, thiazolyl, pyrazolyl, oxazolyl, triazolyl, pyrydyl, quinolynyl, isoquinolyl, pyrimidynyl, pyrazynyl, pyridazynyl, indolynyl, indazolyl, phthalazynyl, naphthyridyl, quinoxalynyl, cinnolynyl, purynyl, pteridynyl, carbazolyl, or acridynyl groups. These aromatic radicals can be unsubstituted or, depending on the nature of the aromatic radical, can carry from one to three, preferably one, identical or different substituent(s), such as those mentioned above in respect of the aromatic radicals $R^a$ and $R^b$.

The aldehydes II $R^a$CHO     (II)

and III $R^b$CHO,    (III)

serving as starting material for the preparation of acyloins of the formula I can be the same or different. If aldehydes are used which have identical radicals $R^a$ and $R^b$, only one acyloin product of the formula I is formed as the product of the reaction. If aldehydes II and III having different radicals $R^a$ and $R^b$ are caused to react with each other in the process of the invention, up to four different reaction products can be obtained. This is illustrated below, by way of example, with reference to the reaction of the invention involving furfurol and benzaldehyde. In this case there are formed in addition to benzoin of the formula VIII

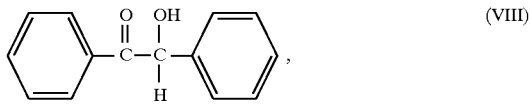

and furoin of the formula IX

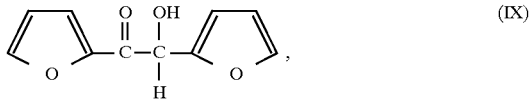

which are in each case formed by autocondensation of two molecules of benzaldehyde or furfurol, additionally the isomeric, crossed acyloins of the formulas X

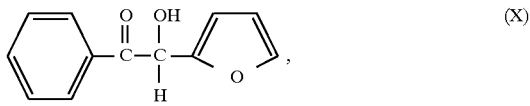

and XI

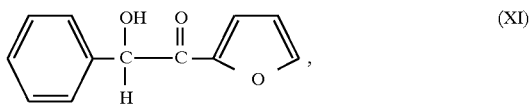

which are formed by the crossed condensation of furfurol and benzaldehyde. Analogous results are generally obtained by the reaction of other aldehydes II and III containing different radicals $R^a$ and $R^b$.

The different products which are formed in the reaction of two different aldehydes II and III in the process of the invention, can be separated from each other in conventional manner, for example by crystallization or distillation or by means of chromatographic methods, such as preparative gas or liquid chromatography. The amounts in which these different reaction products are formed in relationship to each other during crossed condensation, is generally governed by the nature and reactivity of the aldehydes II and III used.

For the purpose of virtually exclusive preparation of a specific crossed acyloin Ia, the aldehyde $R^b$CHO is advantageously first of all incubated with the triazolium catalyst IV in the absence of an auxiliary base, during which process triazolium salt/aldehyde adducts IVa form, in which $R^{2'}$ is the group $R^b$CH(OH). These adducts are advantageously caused to react, in the presence of an auxiliary base, in from 1 to 5 times, preferably in from 1 to 2 times, the stoichiometric amount, more preferably in the stoichiometric amount, with the relevant aldehyde $R^a$CHO. Depending on the nature of the different aldehydes $R^b$CHO and $R^a$CHO used in each case, a wide variety of crossed acyloins can be produced in this way at a high degree of selectivity. The incubation of the triazolium salt IV with the aldehyde $R^b$CHO can be carried out under the same reaction conditions (such as temperature, solvents, etc) as the acyloin condensation itself, which is started, following incubation, by the addition of the auxiliary base. An incubation time of a few minutes is usually sufficient for the formation of IVa, but the incubation time can be increased virtually unlimitedly, if desired.

It has been found, as part of the present invention, that alicyclic or heteroalicyclic acyloins can also be produced with the assistance of the process of the invention by the reaction of aliphatic or heteroaliphatic dialdehydes with the triazolium catalysts of the invention.

The preparation of alicyclic acyloins is preferably effected using aliphatic α,ω-dialdehydes having a total of from 5 to 12, preferably from 5 to 7 carbon atoms, for example, α,ω-pentanedial (glutardialdehyde), α,ω-hexanedial, α,ω-heptanedial, α,ω-decanedial, or α,ω-dodecanedial. The dialdehydes can be branched, but preferably unbranched dialdehydes are used. The alkylene chain of the dialdehydes can carry substituents, such as those mentioned in respect of the aliphatic radicals $R^a$ and $R^b$, provided they do not sterically hinder the intramolecular acyloin condensation of these dialdehydes to cyclic acyloins. Preferred substituents are, eg, $C_1$–$C_4$ alkyl groups, halogen atoms, such as fluorine, chlorine, bromine or iodine atoms, preferably fluorine, chlorine or bromine atoms, the hydroxyl group, the nitro group, the nitrile group, or $C_1$–$C_4$ alkoxy groups. The number of these substituents can be one or two, in particular one, but preferably unsubstituted dialdehydes are used. During the acyloin condensation carried out as proposed in the invention cyclic acyloins form from these dialdehydes which have a number of ring members corresponding to the number of the carbon atoms in the dialdehyde used.

For example, OHC is obtained during the reaction of glutardialdehyde of the formula XII

$$CH_2-CH_2-CH_2-CHO, \quad (XII)$$

with the catalysts of the invention 2-hydroxycyclopentanone of the formula XIII

(XIII)

ie the second aldehyde group in the dialdehyde molecule adds intramolecularly to the first aldehyde function of the dialdehyde, under the action of the catalysts of the invention, ie analogously to the intermolecular condensation of an aldehyde $R^aCHO$ II with an aldehyde $R^bCHO$ III.

The preparation of alicyclic acyloins can alternatively be effected using dialdehydes in which one of the methylene groups of the dialdehyde is replaced by an —O—, —S—, or —N($R^c$)— group, in which $R^c$ stands for a $C_1$–$C_4$ alkyl or acyl group, such that the dialdehyde used can have from 4 to 11, preferably from 5 to 6, carbon atoms in addition to one of the hetero groupings mentioned above. In the process of the invention, heterocycloaliphatic acyloins are formed from these dialdehydes of which the number of ring members corresponds to the number of carbon atoms plus the hetero atoms present in the alkylene chain. For example, there is formed from 3-oxaglutardialdehyde of the formula XIV

$$OHC-CH_2-O-CH_2-CHO, \quad (XIV)$$

the heterocycloaliphatic acyloin of the formula XV

(XV)

The aldehydes $R^aCHO$ II and $R^bCHO$ can be used either as such or in the form of compounds which form aldehydes under the reaction conditions of the process of the invention, ie, compounds which are in equilibrium with the free aldehyde under the reaction conditions. Examples of such aldehyde-forming compounds are, eg, the hemiacetals of the aldehydes II and III with aliphatic or aromatic alcohols, preferably primary $C_1$–$C_{20}$, particularly $C_1$–$C_4$ alcohols. If one of the aldehydes $R^aCHO$ or $R^bCHO$ is formaldehyde, formaldehyde-forming compounds can be used, such as paraformaldehyde, instead of formaldehyde. The dialdehyde starting compounds for the preparation of cyclic acyloins can be used in the form of their hemiacetals, if desired.

The process of the invention is carried out in the presence or absence of a solvent. Suitable solvents comprise, basically, a very broad spectrum of solvents, such as alcohols, eg, methanol, ethanol, propanol, cyclohexanol, 2-ethylhexanol, and hexadecylalcohol, amides, eg, dimethyl formamide (DMF), dibutyl formamide, ureas, such as dimethylethylene urea or dimethylpropylene urea, carbonates, eg, propylene carbonate or ethylene carbonate, aromatic solvents, eg, toluene or xylene, heterocyclics, eg, pyridine, N-methylimidazole, or N-methylpyrrolidone, ketones, eg, acetone, esters, eg, ethyl acetate, ethers, eg, methyl-tert-butyl ether, diethylene glycol dimethyl ether, dimethoxy ethane, tetrahydrofuran, or dioxane, aromatic nitro compounds, eg, nitrobenzene or nitrotoluene, tertiary amines, eg triethylamine, halogenated hydrocarbons such as chloroform, dichloromethane, chlorobenzene, or dichlorobenzene, sulfoxides, such as dimethyl sulfoxide, sulfones, such as dimethyl sulfone or sulfolane, and nitriles, eg, acetonitrile or propionitrile.

The amount of solvent used is not generally critically important and depends on the nature of the solvent used, for which reason the optimum amount of solvent to be used is advantageously determined in a trial run for each solvent. A large number of bases can be used as auxiliary bases for the activation of the triazolium salts IV, which, on account of their bacisity, are capable of deprotonizing the triazolium salts IV in position 5 or the adducts of the triazolium salts IV with the aldehyde $R^bCHO$, also the triazolium salts IVa. In this process non-nucleophilic bases are preferably used, for example, tertiary amines having from 3 to 30 carbon atoms or tertiary cyclic amines, in particular also cyclic amidines.

Suitable tertiary amines are for example, trimethylamine, triethylamine, tripropylamine, tributylamine, ethyldiisopropylamine, decyldiethylamine, tridecylamine, quinuclidine, diazabicyclo[2,2,2]octane, N-methylpiperidine, N-ethylpiperidine, N-propylpiperidine, N-butylpiperidine, N,N-dimethylpiperazine, N-methylmorpholine, dimethylbenzylamine, dibenzylmethylamine, benzyldioctylamine, benzyldiethylamine, cyclohexyldiethylamine, dicylcohexyldiethylamine, dicyclohexylmethylamine, dicyclohexylmethylamine, dicyclohexylethylamine, etc. In particular, triethylamine is preferably used. Of the cyclic amidines, 1,5-diazabicyclo[4,3,0]non-5-ene, 1,8-diazabicyclo[5,4,0]undec-7-ene and 1,5,7-triazabicyclo[4,4,0]dec-7-ene are preferably used.

Alternatively, polymeric tertiary amines can be used as auxiliary bases, for example, cross-linked styrene/divinylbenzene resins or phenol/formaldehyde resins which carry side chains containing tertiary amino groups or whose aryl groups are substituted by dialkylamino groups. Such polymeric amines are usually used as anion exchangers.

In addition, aromatic nitrogen bases can be used, if desired, such as quinoline, pyridine or N-alkylimidazoles, particularly N-($C_1$–$C_4$ alkyl)imidazoles for deprotonizing the triazolium salts I. In addition inorganic bases can be employed, such as alkali metal and alkaline earth metal hydrogen carbonates, alkali metal and alkaline earth metal carbonates, or alkali metal carboxylates, in particular the sodium and potassium salts of $C_1$–$C_4$ carboxylic acids.

It is possible, by using polymeric tertiary amines in the form of anion exchangers, to prepare from the triazolium salts IV solutions of the ylides VI/carbenes VII which contain no auxiliary base. To achieve this, it is merely necessary to deprotonize the triazolium salts IV over an anion exchanger resin carrying tertiary amino groups, for example, by passing a solution of the triazolium salt IV over such an anion exchanger resin, and adding the aldehydes II and III to the solution of the ylide VI/carbene VII not before this has passed the anion exchanger. This mode of operation has the advantage that side reactions which are catalyzed by the auxiliary base, eg, aldol condensations, are greatly suppressed.

If the alcoholate or thiolate adducts of the general formula V or the ylides VI/carbenes VII produced from these compounds by thermal elimination are used as catalysts, the reaction of the invention can be carried out in the absence of an auxiliary base. However the alcoholate or thiolate adducts V are produced in the presence of a base from the corresponding triazolium salts IV by their reaction with the corresponding alcohol or thiol.

In the process of the invention, the aldehydes II and III can be used in the form of the free aldehyde or in the form of aldehyde-forming compounds, eg, in the form of their oligomers, as aldehyde hemiacetals with $C_1$–$C_{20}$, preferably $C_1$–$C_{10}$, particularly $C_1$–$C_4$, alcohols. The aldehydes can be passed to the reaction mixture in gaseous form or in the form of a solution. The aldehydes are generally caused to react at temperatures in the range of from 0° to 200° C., preferably at a temperature of from 10° to 160° C. and more preferably at a temperature of from 20° to 150° C. together with the triazolium salt catalyst and optionally an organic solvent. If the catalyst is produced in accordance with process variant β) from the addition compounds of the formula V in situ in the reaction mixture, temperatures of from 20° to 180° C., preferably of from 60° to 150° C., are generally used. If on the other hand use is made of the catalytically active triazolium compounds produced in accordance with process variant γ) in a separate thermolysis stage, the process can be carried out at temperatures of from 0° to 160° C., preferably from 20° to 120° C.

The pressure employed is not generally of critical importance to the process of the invention. The process is therefore advantageously carried out at atmospheric pressure or under the autogenous pressure of the reaction system.

The molar ratio of the sum of the aldehydes $R^a$CHO II and $R^b$CHO III to the catalyst can be in a range of from 10:1 to 10,000:1 in all embodiments of the process of the invention. In the case of aldehyde-to-catalyst molar ratios of more than 200:1 a base or a buffer can be advantageously added for the purpose of binding acids which may form as products of side reactions. In the preparation of cyclic acyloins from the corresponding dialdehydes a molar ratio of dialdehyde to catalyst of from 10:1 to 10,000:1 is also generally used.

In the preparation of crossed acyloins from different aldehydes $R^a$CHO and $R^b$CHO a molar ratio of $R^a$CHO to $R^b$CHO of from 1:1 to 10:1, preferably a molar ratio of 1:1, is generally used.

As mentioned above, no auxiliary base is required for carrying out the process of the invention in accordance with process variant β) or γ), basically, since the catalysts are produced either in situ (variant β) or ex situ (variant γ) by elimination of RXH, preferably by the elimination of methanol, from the precursor compounds V. Since, however, acids can be formed to a minor degree during the reaction as a result of side reactions, for example by the disproportionation of the aldehyde, and these acids can deactivate the catalyst, the addition of small amounts of base can be advantageous, for example bases such as have been mentioned above as being suitable for use as auxiliary bases, in order to buffer or neutralize these acids. This can be particularly favorable when the process is carried out using very small amounts of catalyst. Also in such cases, the amounts of base used can be similar to those mentioned above for variant α). Advantageously however, smaller amounts of base are used. If the aldehydes used or the aldehyde-forming compounds are contaminated with acids, these are advantageously neutralized for the reasons stated above prior to use in the process of the invention or the action of these acids in the process of the invention can be compensated in situ by the addition of an equivalent amount of base.

The triazolium salts IV used in the process of the invention can be prepared by conventional methods, for example by alkylation of mesoionic compounds, for example the N-alkylation of nitron by means of alkyl halides or dialkyl sulfates (cf Busch et al: *Ber.* 38, 4049 (1905)), by oxidative desulfurization of the correspondingly substituted triazoline-5-thiones (cf Z. *Naturforsch.* B, 25, 1421 (1970); *J. Prakt. Chem.*, 330, 325 (1988)), which can in turn be obtained by the Lewis acid-catalyzed cyclization of the corresponding thiosemicarbazones, which can be prepared from the corresponding isothiocyanates following their reaction with an alkyl or aryl hydrazine to form the relevant thiourea and alkylation thereof with an aldehyde, (*Ber.* 42, 4596 (1909); *Ber.* 34, 320 (1901)). Triazolium salts IV, in which $R^4$ is an ether or thioether group attached to the triazolium ring via the hetero atom, are likewise synthesized starting from the corresponding isocyanates or isothiocyanates by the reaction thereof with a hydrazine to form the corresponding urea or thiourea derivative, followed by formylation and cyclization with formic acid and subsequent alkylation of the 1,2,4-triazolin-5-one or 1,2,4-triazoline-5-thione obtained with an alkylating agent (cf *Ber.* 42, 4596 (1909); *J. Prakt. Chem.* 67, 246 (1903); *J. Prakt. Chem.* 67, 263 (1903)).

Polycyclic triazolium salts IV can be prepared from secondary methylamines after N-nitrosation (*Org. Synth.*, Coll. Vol 2, 460 (1943)) and O-alkylation thereof to form the corresponding alkoxy diazenium salt in a 1,3-dipolar cycloaddition involving the relevant N-heterocyclene (cf *Chem. Ber.* 102, 3159 (1969)).

Triazolium salts IV, which carry a hydrogen atom in position 3 can be obtained, eg, in accordance with the process described in U.S. Pat. No. 3,488,761 by the reaction of 1,2,4-triazole with alkylating or arylating agents, such as alkyl halides or dialkyl sulfates or aryl halides, in particular aryl fluorides. 1,2,4-triazole can be obtained, eg, by the process proposed by Ainsworth et al *J. Am. Chem. Soc.* 77, 621 (1955). Alternatively 3(H)-triazolium salts IV can be obtained by the process proposed by Boyd et al *J. Chem. Soc.* (C) 409 (1971) by the reaction of the corresponding oxadiazolium salts with a primary amine.

To produce the addition compounds V, generally the relevant triazolium salt IV is caused to react in a solvent, for example an ether such as tetrahydrofuran, dioxane or dimethoxy ethane or an alkanol, with the relevant alkanolate or thiolate RXMe, in which Me is the gramm-equivalent of a metal cation, preferably of an alkali metal cation, and X and R have the aforementioned meanings. The alkanolates are preferably used dissolved in the alcohol from which they have been produced. In the reaction of the alkanolates or thiolates RXMe with the triazolium salt IV, the process is generally carried out at temperatures of from 0° to 100° C., preferably from 20° to 50° C., and a molar ratio of alcoholate or thiolate to triazolium salt IV generally of from 0.8:1 to 1.5:1, preferably of from 1:1 to 1.2:1. The addition products V can be isolated from the reaction mixture thus prepared following removal of the solvents used and separation of the resulting metal salts which are difficultly soluble in organic solvents, eg by filtration, and can be used as such in the present invention.

For the purpose of the preparation of the ylide/carbene VI/VII, the addition compounds V are heated to temperatures of from 50° to 160° C., preferably from 60° to 140° C., and more preferably from 70° to 120° C. in substance or in an inert, high-boiling solvent, eg, a paraffin or a sulfone, such as sulfolane (tetrahydrothiophene-1,1 dioxide), until all of the alkanol or thiol RXH has become eliminated from V. This process can be carried out under the autogenous pressure of the reaction system, but it is preferably carried out under reduced pressure. The thermolysis product obtained from this thermolysis can be used directly as catalyst in the process of the invention.

In view of the fact that the autocondensation of formaldehyde using triazolium catalysts IV gives a completely different range of products than when use is made of thiazolium catalysts, a fact due to sterical hindering and differences in reactivity between triazolium and thiazolium catalysts, it is very surprising that aldehydes other than formaldehyde can also be converted to acyloins using the catalysts of the invention.

EXAMPLES

Preparation of the Catalysts

The triazolium salts IV A, IV B, IV C, and IV D were prepared as proposed by Eicher et al (*Chem. Ber.* 102, 3159 (1969)).

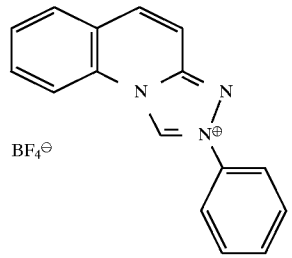

IV A

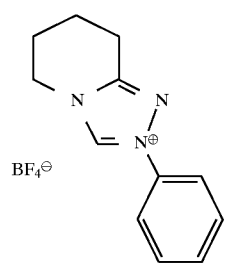

IV B

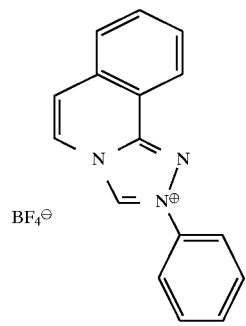

IV C

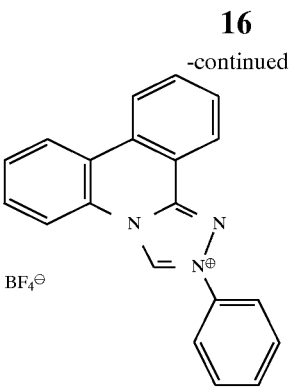

IV D

The triazolium salt IV E was prepared as follows, starting from N,N-diphenyl-N-aminothiourea (prepared in accordance with *Ber.* 42, 4596 (1909)):

3.6 g (82 mmol) of freshly distilled acetaldehyde were added slowly and with external cooling to 20 g (82 mmol) of N,N-diphenyl-N-aminothiourea. The reaction mixture first turned viscous and then solidified.

The product thus obtained was not purified further, but was taken up in 400 mL of ethanol and admixed with a solution of 19.7g (96mmol) of iron(III) chloride in 50 mL of ethanol at 60° C. On completion of the addition stirring was continued for a further 1 h at 60° C. and the ethanol was removed under reduced pressure by distillation. The residues were dissolved in diethyl ether, and the ethereal phase was washed a number of times with water and dried over sodium sulfate. The solvent was removed, by distillation, and the residues were recrystallized from petroleum spirit.

1,4-diphenyl-3-methyl-1,2,4(5H )-triazoline-5-thione:

mass spectrum: molar peak 267 m/e; melting point: 128° to 130° C.; correct $^1$H— and $^{13}$C-NMR spectra.

4.0 g (1 5 mmol) of 1,4-diphenyl-3-methyl-1,2,4(5H)-triazoline-5-thione were stirred with 60mL of concentrated nitric acid, 60mL of water, and 14 mL of concentrated perchloric acid, at room temperature. Following a reaction time of a few minutes solids began to precipitate. On completion of the reaction the solids were removed by filtration, washed successively with water, ethanol, and diethyl ether and dried under reduced pressure.

1,4-diphenyl-3-methyl-1,2,4-triazolium perchlorate IV E:

melting point: 218° C. (decomposition); correct $^1$H— and $^{13}$C-NMR spectra

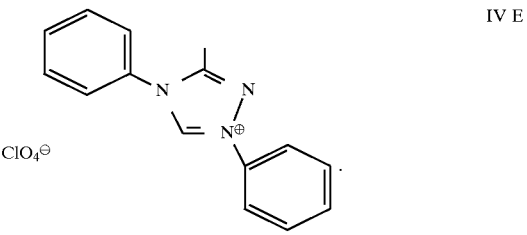

IV E

The triazolium salt IV F was prepared following the prepublished process cited in the description above (Z. *Naturforsch.* B, 25, 1421 (1970); *J. Prakt. Chem.*, 330, 325 (1988)) via the 2,3,4-triphenyl-substituted 1,2,4-triazoline-5-thione derivative

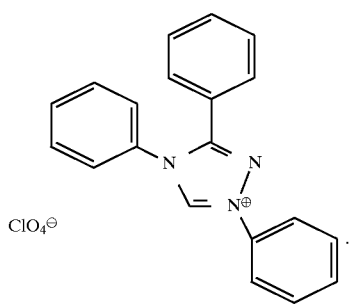

IV F 1,3,4-Triphenyl-5-hydroxymethylene-1,2,4-triazolium perchlorate IV G:

5.0g (12.5 mmol) of IV F, 4.0 g (133 mmol) of paraformaldehyde and 130 mL of tetrahydrofuran were heated to 80° C. for 1 h in a glass autoclave. After cooling, the solvent was removed, by distillation under reduced pressure, and the semisolid residues were stirred with 10 wt % strength perchloric acid. The solidified residues were washed with water until neutral and recrystallized from ethanol.

Melting point: 182° to 183° C., correct $^1$H— and $^{13}$C-NMR sprectra

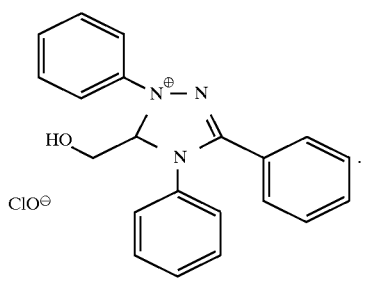

IV G 2,4-Diphenyl-5-(N-methyl-N-phenylamino)-1,2,4-triazolium iodide IV H:

Nitron was prepared according to Ber. 38, 4049 (1905) and caused to react with methyl iodide by the process stated therein to give IV H

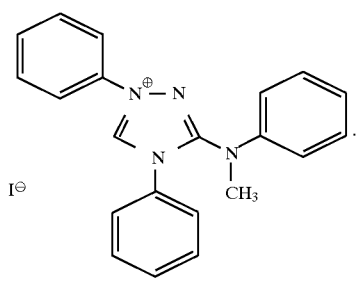

IV H 2.0 g (4.4 mmol) of IV H were dissolved in 40.0 g of tetrahydrofuran together with 5.3 g (176 mmol) of paraformaldehyde under a blanket of argon at 55° C. and refluxed for 5 h. The solids which separated were removed by filtration with heating. The organic solution was diluted with 100 mL of dichloromethane, washed a number of times with water and dried over magnesium sulfate. Separation of the solvents under reduced pressure gave 1,4-diphenyl-5hydroxymethylene-3-(N-methyl-N-phenylamino)-1,2,4-triazzolium iodide IV I:

Melting point: 200° C.; correct $^1$H— and $^{13}$C-NMR spectra

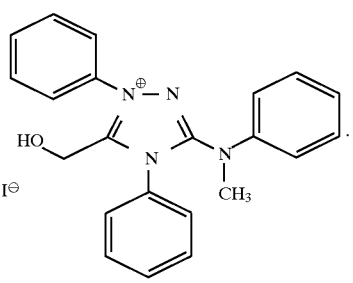

IV I 1,4-Diphenyl-3-(N-dodecyl-N-phenylamino)-1,2,4-triazolium iodide IV J:

2.0g (6.4mmol) of nitron and 9.5 g (32 mmol) of dodecyl iodide were heated to 100° C. in 10 mL of toluene over a period of 24 h under a blanket of argon. The precipitated crystalline product was removed from the cooled solution by filtration and recrystallized from ethanol/water.

Melting point: 129° to 130° C.; correct $^1$H— and $^{13}$C-NMR spectra

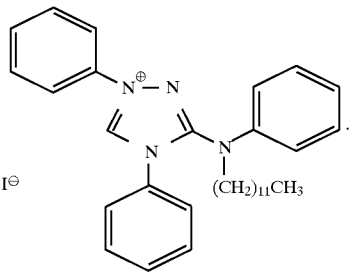

IV J 1,4-Diphenyl-3-methoxy-1,2,4-triazolium tetrafluoroborate IV K:

2.0 g (8.4 mmol) of 1,4-diphenyl-3-hydroxy-1,2,4-triazolium hydroxide internal salt (prepared after J. Prakt. Chem. 67, 263 (1 903)) were suspended in 50 mL of dichloromethane. 1.3 g (9.2 mmol) of solid trimethyloxonium tetrafluoroborate were slowly added to this suspension at 0° C. The reaction mixture was stirred for a further 4 h at 0° C. The solids were then removed by filtration, washed with dichloromethane and recrystallized from ethanol. IV K was obtained in the form of a mixture consisting of 58 wt % of IV K, 23 wt % of the starting compound, and 19% of diphenyl-2-methyl-1,2,4-(3H)-triazolinium-3-one:

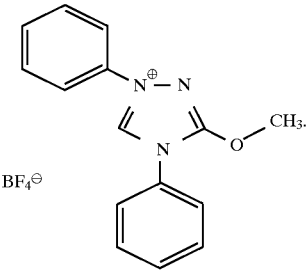

IV K

Compound IV L was prepared by the process proposed in J. Prakt. Chem. 67, 246 (1903).

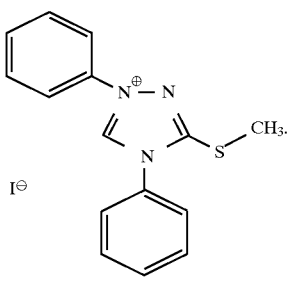

1,3,4-Triphenyl-5-H-5-methoxy-1,2,4-triazoline Va 1.4 g (26 mmol) of sodium methanolate dissolved in 30 mL of methanol were added to a solution of 7.0 g (25 mmol) IV F in 150 mL of methanol at room temperature. The methanol was then evaporated off under reduced pressure and the residues taken up in diethyl ether. The undissolved residues consisting of sodium perchlorate were removed by filtration. The solids remaining after removal of the solvent were recrystallized from methanol.

Melting point: 136° to 137° C.; correct $^1$H— and $^{13}$C-NMR spectra

Ylide/carbene VIa/VIIa

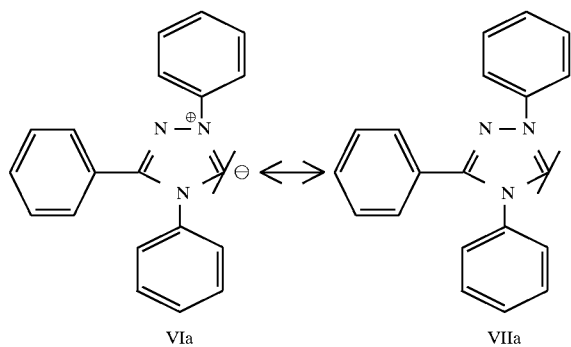

1.0 g (3 mmol) of Va was heated at 80° C. under reduced pressure, until the weight loss calculated for the elimination of methanol had occurred. This was so following a period of 16 h.

1-p-Nitrophenyl-4-methyl-1,2,4-triazolium iodide IV M 5.0 g (2.6 mmol) of 2-p-nitrophenyl-1,2,4-triazole, 4.1 g (29 mmol) of methyl iodide, and 20 mL of DMF were stirred over a period of 24 h at 100° C. in a glass autoclave. Following removal of the solvent, the residues were taken up in 100 mL of dichloromethane, and the mixture was stirred for 30 min and the precipitated solids removed by filtration:

Melting point: 213° to 216° C.; correct 1H— and $^{13}$C-NMR spectra

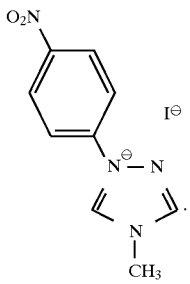

Example 1

Mixture of 152 g of n-heptanal and 1.52 g (1 wt %) of 5-methoxy-1,3,4-triphenyl-4,5-dihydro-1,2,4-triazole (Va) was heated over a period of 2 h at 130° C. under autogenous pressure. The conversion, as determined by gas-chromatographic analysis, was 61% and the selectivity toward 8-hydroxy-7-tetradecanone was 99%.

Examples 2 to 8

Examples 2 to 8 were carried out in a manner similar to that described in Example 1 with variation of the temperature of reaction and the reaction time. The analysis of these experiments are listed in the table below.

| Example | Temperature [°C.] | Time [min] | Conversion [%] | Selectivity [%] |
|---|---|---|---|---|
| 2 | 110 | 120 | 40 | 95 |
| 3 | 120 | 120 | 53 | 96 |
| 4 | 130 | 60 | 48 | 98 |
| 5 | 130 | 120 | 61 | 99 |
| 6 | 140 | 120 | 59 | 94 |
| 8 | 150 | 120 | 58 | 92 |

Example 9

1.44 kp of n-butyraldehyde and 13 g of catalyst Va were heated to 130° C. in an autoclave under autogenous pressure for 2 h. GC-analysis or the effluent gave a conversion of 50% and a selectivity toward butyroin of 94%. The effluent was worked up by vacuum distillation. There were obtained 673 g of butyroin (5-hydroxy-4-octanone), equivalent to a yield of 47%.

Examples 10 to 16

In a manner similar to that described in Example 1, the following educt aldehydes were heated to 130° C. together with 1 wt % of catalyst Va, based on educt used, for a period of 2 h. The conversion (C) and selectivity (S) of the reaction were determined by gas chromatography.

| Example | Educt | Product | C/S [%] |
|---|---|---|---|
| 10 | acetaldehyde | acetoin | 90/95 |
| 11 | glyoxal mono-neopentyl-glycol acetate | 2-oxo-3-hydroxy-succinate hyde bis(neopentylglycol acetal) | 70/66 |
| 12 | 5-methyl formylvalerate | 6-methyl hydroxy-7-dodecanonedicarboxylate | 60/80 |
| 13 | benzaldehyde | benzoin | 47/98 |
| 14 | p-anisaldehyde | 4,4'-dimethoxybenzoin | 22/90 |
| 15 | furfurol | furoin | 69/93 |
| 16 | pyridine-2-aldehyde | 2,2'-pyridoin | 84/85 |

Example 17

89 g (0.5 mol) of glyoxal mononeopentylglycol acetal in the form of the hemiacetal with n-butanol were admixed with 1.64 g (1 mol %) of the catalyst Va and a stream of nitrogen was passed through this solution at 25° C. over a period of 20 min. The reaction was then caused to take place at 80° C. with stirring over a period of 2 h. At a conversion of 70% the selectivity toward 2-oxo-3-hydroxysuccinaldehyde bis-n-pentylglycol acetal was 92%.

Example 18

10 g (0.1 mol) of acetoxyacetaldehyde were dissolved in 50 g of tetrahydrofuran and a stream of nitrogen was passed through this solution for a period of 20 min.

Following the addition of 0.33 g (1 mol %) of the catalyst Va the solution was refluxed over a period of 6 h. At a conversion of 55% the selectivity toward 1,4-diacetoxy-3-hydroxy-2-butanone was 12% and the selectivity toward 1,3,4-triacetoxy-2-butanone was 36%.

Example 19

30 g (0.25 mol) of methyl glyoxylate in the form of its hemiacetal with methanol were admixed with 150 g of tetrahydrofuran and 0.82 g (1 mol %) of catalyst Va and the mixture was refluxed for 2 h under a blanket of nitrogen. At a conversion of 90% the selectivity toward methyl dihydroxymaleate, the enol form of acyloin, was 99%. After cooling, the product crystallized out in a yield of 30%.

Melting point: 165° C.

Example 20

A mixture of 10 g of furfurol and 0.1 g of catalyst Va was stirred over a period of 1 h at 20° C. During this period the reaction mixture turned crystalline. At a furfurol yield of 93% the selectivity toward furoin was 95%.

Example 21

300 mL (336.8 g) of a ca 50% strength aqueous glutardialdehyde solution and 300 mL of cyclohexane were dehydrated in a water separator by azeotropic distillation. Following withdrawal of the residual cyclohexane in a rotary evaporator, the residues consisting of anhydrous glutardialdehyde (159.9 g ≙ 1.59 mmol) were dissolved in 700 mL of acetonitrile. To this solution there were added 5.23 g (15.9 mmol) of catalyst Va and the mixture was refluxed over a period of 5 h. The solvent was then removed in a rotary evaporator and the residues were distilled under reduced pressure. There were obtained 103.2 g (64.9% yield) of 2-hydroxycyclopentanone XIII.

Example 22

89 g (0.5 mol) of glyoxal mononeopentylglycol acetal in the form of the hemiacetal with n-butanol were admixed with 1.64 g of catalyst Va and 15 g (0.5 mol) of formaldehyde. A stream of nitrogen was passed through the solution over a period of 20 min. The mixture was then stirred for 2 h at 80° C. At a conversion of 75% the selectivity toward the mixture of the neopentylglycol acetals of 2-oxo-3-hydroxypropionaldehyde and 2-hydroxy-3-oxopropionaldehyde was 30%.

Example 23

A mixture of 140 g (1 .33 mol) of benzaldehyde and 20 g (0.66 mol) of paraformaldehyde was admixed with 0.54 g of catalyst Va and was heated at 80° C. for 90 min under a blanket of nitrogen. At a benzaldehyde yield of 45% the selectivity toward 2-hydroxy-2-phenylacetaldehyde was 80%.

Example 24

2.9 g (0.03 mol) of furfurol and 10.6 g (0.15 mol) of n-butyraldehyde were admixed with 0.13 g of the catalyst Va and heated to 130° C. over a period of 1 h in an autoclave under a blanket of nitrogen. At a furfurol yield of 100% the selectivity toward the formation of the mixture of 1-(1-furyl)-1-hydroxy-2-pentanone und 1-(1-furyl)-2-hydroxy-1-pentanone was 60%.

We claim:

1. A process for the preparation of acyloins except for autocondensation products of formaldehyde of the formula I

in which $R^a$ and $R^b$ are the same or different and stand for hydrogen or an optionally substituted $C_1$–$C_{20}$alkyl, an optionally substituted $C_6$–$C_{10}$aryl, an optionally substituted $C_7$–$C_{12}$aralkyl, an optionally substituted heteroaryl, or an optionally substituted heterocycloalkyl group, wherein an aldehyde of the formula II

is reacted with an aldehyde of the formula III

in which $R^a$ and $R^b$ have the above meanings and at least one of the radicals $R^a$ and $R^b$ denotes a radical other than hydrogen, in the presence of a catalyst produced, with the assistance of an auxiliary base, from a triazolium salt of the formula IV

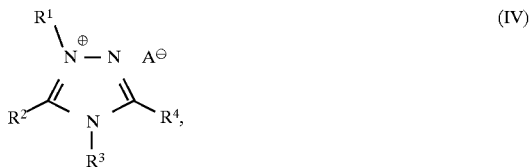

in which $R^1$ and $R^3$ are the same or different and stand for aliphatic groups having from 1 to 30 carbon atoms, optionally substituted aryl groups, optionally substituted aralkyl groups and/or optionally substituted heteroaryl groups, $R^2$ denotes hydrogen or the group $R^b$CH(OH)

and in which $R^4$ denotes hydrogen, a halogen atom, a nitro or cyano group, an aliphatic group having from 1 to 30 carbon atoms, an optionally substituted aryl group, an optionally substituted aralkyl group, an optionally substituted heteroaryl group, an alkoxy group —$OR^5$, a thioether group —$SR^6$, an amino group —$NR^7R^8$, an acyl group —$COR^9$ or an ester group —$COOR^{10}$, where the radicals $R^5$, $R^6$, $R^7$, $R^8$, and $R^9$ stand for radicals as mentioned above with respect to $R^1$, and $R^{10}$ is a $C_1$–$C_{30}$ alkyl or an optionally substituted aryl or aralkyl group, or in which $R^3$ and $R^4$ together form a $C_3$–$C_5$ alkylene, $C_3$–$C_5$ alkenylene, $C_6$–$C_{14}$ arylene, $C_7$–$C_{14}$ aralkylene, or $C_8$–$C_{14}$ aralkenylene bridging member, and A is the equivalent of an anion carrying one or more negative charges for the electrical neutralization of the charge on the triazolium cation.

2. A process as defined in claim 1, wherein the aldehydes of the formulas II and III are reacted with a catalyst which has been prepared, with the assistance of an auxiliary base, from a triazolium salt of the formula IV

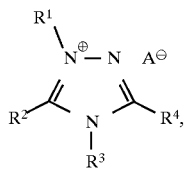

(IV)

in which
R$^1$ and R$^3$ are the same or different and stand for C$_1$–C$_{30}$ alkyl groups, C$_2$–C$_{30}$ alkenyl or C$_2$–C$_{30}$ alkynyl groups having 1 or 2 multiple bonds, C$_3$–C$_{20}$ cycloalkyl, C$_3$–C$_{20}$ alkenyl groups, C$_3$–C$_{20}$ heterocycloalkyl, C$_3$–C$_{20}$ alkenyl groups, C$_2$–C$_{30}$ alkoxy groups having one or more oxygen atoms in the ether chain and attached to the triazolium ring via a carbon atom, C$_1$–C$_{30}$ fluorine, chlorine or bromine-containing haloalkyl groups having one or more halogen atoms, C$_2$–C$_{30}$ secondary amino groups, C$_3$–C$_{30}$ tertiary amino groups attached to the triazolium ring via a carbon atom, optionally substituted C$_6$–C$_{14}$ aryl groups, optionally substituted C$_6$–C$_{14}$ aralkyl groups, optionally substituted C$_7$–C$_{20}$ aralkyl groups, optionally substituted C$_2$–C$_{15}$ heteroaryl groups having from 1 to 3 nitrogen atoms or one oxygen or sulfur atom or having 1 or 2 nitrogen atoms and one oxygen or sulfur atom in the ring, R$^2$ represents the group R$^b$CH(OH), and in which the radical R$^4$ is the same as, or different from, the radicals R$^1$ or R$^3$ or stands for a hydrogen atom, a nitro or cyano group, a fluorine, chlorine or bromine atom, an alkoxy group —OR$^5$ attached to the triazolium ring via the oxygen atom, a thioether group —SR$^6$ attached to the triazolium ring via the sulfur atom, an amino group —NR$^7$R$^8$ attached to the triazolium ring via the nitrogen atom, an acyl group —COR$^9$ or an ester group —COOR$^{10}$, where the radicals R$^5$, R$^6$, R$^7$, R$^8$ and R$^9$ stand for radicals as mentioned above for R$^1$, and R$^{10}$ is a C$_1$–C$_{30}$ alkyl or an optionally substituted aryl or aralkyl group, or in which R$^4$ and R$^3$ together form a C$_3$–C$_5$ alkylene, C$_3$–C$_5$ alkenylene, C$_6$–C$_{14}$ arylene, C$_7$–C$_{14}$ aralkylene, or C$_8$–C$_{14}$ aralkenylene bridging member, and A is the equivalent of an anion carrying one or more negative charges for the electrical neutralization of the charge on the triazolium cation.

3. A process as defined in claim 1, wherein a catalyst is used which has been produced by the elimination of compounds RXH from a compound of the formula V

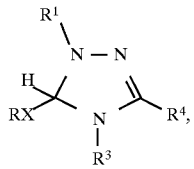

(V)

in which

X stands for oxygen or sulfur and

R is a C$_1$–C$_4$ alkyl group and

R$^1$, R$^3$ and R$^4$ have the meanings stated in claim 1.

4. A process as defined in claim 1, wherein a catalyst is used which has been produced by the elimination of methanol from a compound of the formula Va

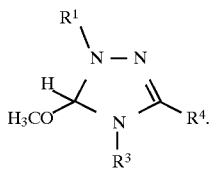

(Va)

5. A process as defined in claim 1, wherein a catalyst is added to the reaction mixture which has been previously produced in a separate reaction by thermal elimination of compounds RXH from a compound of the formula V.

6. A process as defined in claim 1, wherein a catalyst is added to the reaction mixture, which has been previously produced in a separate reaction by thermal elimination of methanol from a compound of the formula Va.

7. A process as defined in claim 1, wherein aldehydes of the formulas II and III are used which have identical radicals R$^a$ and R$^b$.

8. A process as defined in claim 1, wherein aldehydes of the formulas II and III are used in the form of their hemiacetals with an aliphatic or aromatic alcohol.

9. A process for the preparation of cycloaliphatic or heterocycloaliphatic acyloins having a total of from 5 to 12 ring members, wherein an optionally substituted aliphatic C$_5$–C$_{12}$ dialdehyde or a heteroaliphatic dialdehyde having a chain length of from 4 to 11 carbon atoms, which additionally contains in the chain an —O—, —S— or —N(R$^c$)— group, in which R$^c$ is a C$_1$–C$_4$ alkyl or acyl group, is reacted with a catalyst as defined in claim 1.

10. A process as defined in claim 9, wherein the dialdehydes react in the form of their mono- or bis-hemiacetals with an aliphatic or aromatic alcohol.

11. A process for the preparation of crossed acyloins of the general formula Ia

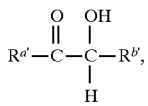

(Ia)

in which the radicals R$^{a'}$ and R$^{b'}$ differ from each other and stand for hydrogen or an optionally substituted C$_1$–C$_{20}$ alkyl, an optionally substituted C$_6$–C$_{10}$ aryl, an optionally substituted C$_7$–C$_{11}$ aralkyl, an optionally substituted heteroaryl, or an optionally substituted heterocycloalkyl group, except for dihydroxy acetone, glyceryl aldehyde, and C$_4$ and C$_5$ sugars, wherein an aldehyde of the formula II

 R$^a$CHO      (II)

is reacted with a triazolium salt of the formula IVa

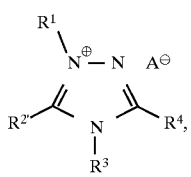

(IVa)

in which

R$^1$ and R$^3$ are the same or different and stand for aliphatic groups having from 1 to 30 carbon atoms, for optionally substituted aryl groups, for optionally substituted aralkyl groups and/or for optionally substituted heteroaryl groups, R$^{2'}$ represents the group R$^b$CH(OH)

and in which

R⁴ is the same as, or different from, the radicals R¹ and R³ or stands for hydrogen, a halogen atom, a nitro or cyano group, an aliphatic group having from 1 to 30 carbon atoms, an optionally substituted aryl group, an optionally substituted aralkyl group, an optionally substituted heteroaryl group, an alkoxy group —OR⁵, a thioether group —SR⁶, an amino group —NR⁷R⁸, an acyl group —COR⁹ or an ester group —COOR¹⁰, where the radicals R⁵, R⁶, R⁷, R⁸ and R⁹ stand for radicals as mentioned above in respect of R¹, and R¹⁰ denotes a $C_1$–$C_{30}$ alkyl group or an optionally substituted aryl or aralkyl group, or in which R³ and R⁴ together form a $C_3$–$C_5$ alkylene, $C_3$–$C_5$ alkenylene, a $C_6$–$C_{14}$ arylene, a $C_7$–$C_{14}$ aralkylene, or $C_8$–$C_{14}$ aralkenylene bridging member, and A is the equivalent of an anion carrying one or more negative charges for the electrical neutralization of the charge on the triazolium cation, in the presence of an auxiliary base and in a molar ratio of triazolium salt IVa to aldehyde II of from 1:1 to 5:1, provided that at least one of the radicals $R^a$ or $R^b$ is other than hydrogen.

12. A process as defined in claim 11, wherein the aldehydes of the formula II are reacted, in the presence of an auxiliary base, with a triazolium salt of the formula IVa

(IVa)

in which

R¹ and R³ are the same or different and stand for $C_1$–$C_{30}$ alkyl groups, $C_2$–$C_{30}$ alkenyl, $C_2$–$C_{30}$ alkynyl groups having 1 or 2 multiple bonds, $C_3$–$C_{20}$ cycloalkyl, $C_3$–$C_{20}$ alkenyl groups, $C_3$–$C_{20}$ heterocycloalkyl, $C_3$–$C_{20}$ alkenyl groups, $C_2$–$C_{30}$ alkoxy groups having one or more oxygen atoms in the ether chain and attached to the triazolium ring via a carbon atom, $C_1$–$C_{30}$ fluorine, chlorine and/or bromine-containing haloalkyl groups having one or more halogen atoms, $C_2$–$C_{30}$ secondary amino groups, $C_3$–$C_{30}$ tertiary amino groups attached to the triazolium ring via a carbon atom, optionally substituted $C_6$–$C_{14}$ aryl groups, optionally substituted $C_6$–$C_{14}$ aralkyl groups, optionally substituted $C_7$–$C_{20}$ aralkyl groups, optionally substituted $C_2$–$C_{15}$ heteroaryl groups having from 1 to 3 nitrogen atoms or one oxygen or sulfur atom or having 1 or 2 nitrogen atoms and one oxygen or sulfur atom in the ring, $R^{2'}$ represents the group $R^b CH(OH)$, and in which the radical R⁴ is the same as, or different from, the radicals R¹ and R³ or stands for a hydrogen atom, a nitro or cyano group, a fluorine, chlorine or bromine atom, an alkoxy group OR⁵ attached to the triazolium ring via the oxygen atom, a thioether group SR⁶ attached to the triazolium ring via the sulfur atom, an amino group NR⁷R⁸ attached to the triazolium ring via the nitrogen atom, an acyl group COR⁹ or an ester group COOR¹⁰, where the radicals R⁵, R⁶, R⁷, R⁸ and R⁹ stand for radicals as mentioned above for R¹, and R¹⁰ is a $C_1$–$C_{30}$ alkyl or an optionally substituted aryl or aralkyl group, or in which R⁴ and R³ together form a $C_3$–$C_5$ alkylene, $C_3$–$C_5$ alkenylene, $C_6$–$C_{14}$ arylene, $C_7$–$C_{14}$ aralkylene, or $C_8$–$C_{14}$ aralkenylene bridging member, and A is the equivalent of an anion carrying one or more negative charges for the electrical neutralization of the charge on the triazolium cation.

* * * * *